United States Patent [19]

Livingston

[11] 4,251,461
[45] Feb. 17, 1981

[54] PROCESS FOR REDUCING ACID IMPURITY LEVELS IN N-(TERTIARYAMINOALKYL)ACRYLAMIDE PRODUCTION

[75] Inventor: David R. Livingston, Austin, Tex.

[73] Assignee: Texaco Development Corporation, White Plains, N.Y.

[21] Appl. No.: 112,759

[22] Filed: Jan. 17, 1980

[51] Int. Cl.³ .................................................. C07C 103/64
[52] U.S. Cl. ...................................... 564/204; 544/86; 544/96; 546/186; 546/208; 546/209; 260/326.25
[58] Field of Search .................... 260/561 N, 326.25; 546/186, 208, 209; 544/86, 96

[56] References Cited

U.S. PATENT DOCUMENTS

| | | | |
|---|---|---|---|
| 2,683,741 | 7/1954 | Wiley | 260/561 N |
| 3,652,671 | 3/1972 | Barron | 260/561 N |
| 3,878,247 | 4/1975 | Moss et al. | 260/561 N |
| 3,883,491 | 5/1975 | Hoke | 260/561 N |
| 3,914,303 | 10/1975 | Daniher et al. | 260/561 N |
| 4,031,138 | 6/1977 | Nieh et al. | 260/561 N |
| 4,180,643 | 12/1979 | Moss et al. | 260/561 N |

Primary Examiner—Arthur P. Demers
Attorney, Agent, or Firm—Carl G. Ries; Robert A. Kulason; Kenneth R. Priem

[57] ABSTRACT

A non-catalytic process for the preparation of N-(tertiaryaminoalkyl)acrylamides is disclosed which comprises subjecting a corresponding β-aminopropionamide to a pyrolysis temperature of about 180° to 300° C. after storage of the β-aminopropionamide in an atmospheric holding tank at a temperature of about 150° to 220° C. from eight to seventy-two hours prior to pyrolysis. The corresponding β-aminopropionamide compounds can be prepared by mixing and reacting at least two moles of a tertiaryaminoalkyl amine with an acrylic acid or ester compound. The inventive process provides the production of the N-(tertiaryaminoalkyl)acrylamides in high yields with minimal back addition or polymerization and greatly reduced acid impurity levels.

10 Claims, No Drawings

PROCESS FOR REDUCING ACID IMPURITY LEVELS IN N-(TERTIARYAMINOALKYL)ACRYLAMIDE PRODUCTION

BACKGROUND OF THE INVENTION

1. Field of the Invention

The present invention relates to a chemical process for making useful cationic vinyl monomers and, more particularly, pertains to an improved non-catalytic process for the preparation of N-(tertiaryaminoalkyl)acrylamides having very low acid impurity levels. The products of this invention are useful in preparing flocculants, adhesion promoters, oil soluble dispersants, epoxy curing agents and ion exchange resins.

2. Description of the Prior Art

The basic process for the production of N-(tertiaryaminoalkyl)acrylamides related to this invention is given in U.S. Pat. No. 3,878,247, in which an acrylic acid or ester is first reacted with excessive tertiary amino alkyl amine to form a $\beta$-aminopropionamide intermediate. Acrylic acid or ester compounds useful in the invention include acrylic acid, methacrylic acid, methyl acrylate, methyl methacrylate, ethyl acrylate and ethyl methacrylate. Temperatures from 170° to 210° C. are employed. The propionamide intermediate is then pyrolyzed at 180° to 300° C. to the desired N-(tertiaryaminoalkyl)acrylamide product and to recyclable tertiary amino alkyl amine.

When the process of U.S. Pat. No. 3,878,247 was scaled up to produce substituted acrylamide products like dimethylaminopropyl methacrylamide (DMAPMA), it was found that there was a level of acrylic acid impurity in the product. Potential polymerization applications for products such as DMAPMA require the highest possible product purities. At the present time, utilizing the method of U.S. Pat. No. 3,878,247, attainment of product acid impurity levels of approximately 0.1 meq/gm, (approximately 0.86 weight percent), which is the maximum allowable for many purposes, requires propionamide reactor batch cycles of up to twelve hours. A water removal and purification tower, as well as reactor pressure requirements, for the initial propionamide reactor system used may dictate that the reactor be expensive in cost. In addition, it was thought that a by-product water removal stream had to be vented at all times to drive the reaction sufficiently. This task was accomplished by carrying out the reaction at the bubble point of the reactor contents.

It is an object of this invention to provide a process for the production of N-(tertiaryaminoalkyl)amides which have a very low acid impurity level in the final product stream. It was surprisingly found that holding the batch or continuously produced propionamide intermediate in an atmospheric tank at 150° to 220° C. immediately prior to continuous pyrolysis at 180° to 300° C., rather than cooling down and re-heating the propionamide intermediate before and after storage, as was the usual method described in U.S. Pat. No. 3,878,247, would reduce the acid impurity level of the final product by at least an entire order of magnitude. Holding the propionamide at an elevated temperature not only allows obvious savings in process utility costs, but also allows for the surprising result of a considerable reduction in the acid impurity content of the final product. Further unexpected advantages are that there is no recognizable yield loss under the closely controlled conditions described, and product stability is improved by a lower acid content.

While acid concentration can be reduced by longer hold times in the initial, pressure rated propionamide reactor, the capital costs of a larger initial reactor are very high compared with a lower cost "post reactor" or surge tank, which is essentially an atmospheric pressure rated storage tank with a small vent condenser. The concept of a lower cost "post reactor" surge or storage tank might thereby allow considerable savings in plant capital costs, as well as providing an increase in the final product purity. Other potentially workable methods of reducing the acid impurity level in the N-(tertiaryaminoalkyl)acrylamide product, such as extraction, are potentially more expensive than the improvement described herein.

SUMMARY OF THE INVENTION

The present invention is an improved, noncatalytic process for the preparation of N-(tertiaryaminoalkyl)acrylamides which comprises subjecting a $\beta$-amino propionamide to a temperature of about 180° C. to about 300° C. in the absence of a catalyst after the $\beta$-aminopropionamide has been stored in a holding tank at a temperature of about 120° C. to about 240° C. and a pressure of about 300 mm Hg to about 1550 mm Hg for about eight to about seventy-two hours. The $\beta$-aminopropionamide is obtained from mixing and reacting at least two moles of a tertiaryaminoalkylamine with one mole of an acrylic acid or ester compound.

DETAILED DESCRIPTION OF THE PREFERRED EMBODIMENTS OF THE INVENTION

The basic process of producing N-(tertiaryaminoalkyl)acrylamides is described in U.S. Pat. No. 3,878,247. Using only this previous technology, propionamide batch cycle times of up to twelve to thirteen hours were required to produce propionamide acid concentrations below 0.15 meq/gm. Lower acid concentrations required longer batch cycles, and/or a larger reactor. Acid concentrations of the final product of DMAPMA were proportional to starting propionamide acid concentrations.

Using the method described in this invention, acid concentrations can be dramatically reduced with the use of a lower cost, insulated, atmospheric pressure rated tank having an optional partial reflux condenser attached to the vent. The crude propionamide product is pumped into the storage tank at the reaction temperature and stored for a chosen average residence time prior to being continuously fed to the pyrolysis reactor in which the reaction to an N-(tertiaryaminoalkyl)acrylamide is conducted. Average residence time is chosen on the basis of the desired level of acid reduction. Use of a simple internal or external tank heater is optional, depending on the average residence time and temperature desired. During the hot storage period, acid reduction is obtained by completion of the ester amide interchange reaction, which produces the desired propionamide intermediate. An average hold time of one to seventy-two hours or more at temperatures above 100° C. might be utilized, with an acid reduction rate increasing with temperature.

Nearly any ratio or combination of initial reactor and hot storage tank or "post reactor" residence times can be chosen, whether the initial reactor is a batch, semibatch or continuous type, as long as sufficient by-product water has been removed prior to hot storage to allow the equilibrium ester amide interchange reaction to proceed favorably. If a completely continuous propionamide reactor preparation scheme is utilized, the hot storage tank may serve as a continuous stirred tank reactor.

Examples illustrating the reduction of acid by use of the "post reactor" storage tank concept are given in the accompanying table for several storage temperature-time combinations. Acid concentrations of the crude substituted propionamide precursor to one particular N-(tertiaryaminoalkyl)acrylamide, DMAPMA, (dimethylaminopropylmethacrylamide) are shown. Post reactor hot storage tank conditions were simulated by storing the normally produced crude propionamide starting material in two to five liter temperature controlled pots equipped with simple water cooled vent condensers. Temperature control was utilized only to make up for high heat losses in the test vessels.

| Ex. No. | Avg. Storage Temp. °C. | Acid Concentrations, meq/gm | | | Notes |
|---|---|---|---|---|---|
| | | Starting | After 24 hrs. | After 41 hrs. | After 48 hrs. | |
| 1 | 208 | 0.073 | 0.014 | — | 0.009 | Unagitated |
| 2 | 180 | 0.08 | 0.018 | — | 0.008 | Unagitated |
| 3 | 188 | 0.14 | — | 0.015 | — | Agitated |

It may be seen from Examples 1 and 2 that after storage of twenty-four hours, the acid concentrations of the propionamide was reduced by a factor of four. The acid concentrations in all examples was reduced by a factor of ten after storage in a heated holding tank for a period of forty-one or forty-eight hours. Longer periods of storage would result in even lower acid concentrations.

To illustrate that the invention disclosed herein results in a low acid final product N-(tertiaryaminoalkyl)acrylamide, approximately 2028 grams of crude substituted propionamide from Example 3 were continuously pryolyzed at 222° to 249° C. A fraction of the pyrolysis overhead obtained was batch distilled to recover a DMAPMA specimen of 98.5% purity by GLC analysis, with only 0.018 meq/gm of acid and a viscosity of 33.3 cs. at 60° F.

EXAMPLE IV

Typical DMAPMA product made from untreated crude propionamide having a 0.14 meq/gm starting acid would contain approximately 0.17 meq/gm acid (or about 1.5 weight percent), and have a viscosity of greater than or equal to 38 cs. at 60° F. As a specific example, analyses taken during a steady pilot plant operation conducted under the process taught by U.S. Pat. No. 3,878,247 revealed a 0.12 meq/gm acid content in normal, untreated crude propionamide. The resultant recovered product from this intermediate had 0.21 meq/gm acid content and a viscosity of 42.1 cs. at 60° F.

While there is a large reduction in the pre-acid content of the propionamide intermediate, which should lead to lower product acid levels, there is no recognizable buildup in polymer content due to storage at the elevated temperature. This fact means that higher product purity can be obtained with no loss of yield. Achieving no yield loss is obtained by carefully choosing the temperature and duration of β-propionamide storage.

In addition, the acid reduction reaction can be accomplished without the use of an expensive overhead water/amine separation system, since the reaction will proceed below the bubble point.

It can be seen that the invention is very useful in allowing production of a high purity monomer product. The lower acid products should perform more adequately in applications such as waste water treatment, coatings, oil additives, etc.

EXAMPLE V

Another advantage of the invention is that the reduced acid monomer also exhibits higher storage stability. Demonstration of this fact may be seen from an example where a portion of DMAPMA having a 0.058 meq/gm acid impurity level was spiked with methacrylic acid to a 0.128 meq/gm acid level. After six months storage at approximately 70° F., the higher acid level aliquot showed markedly lower stability toward polymerization during storage than the companion lower acid aliquot. In addition, lower acid crude propionamide and intermediate monomer product should be less corrosive to process equipment, allowing longer equipment life. Further, the process equipment required by this invention is of lower capital cost than that required under previous technology for a given purity level.

Many modifications and variations of the invention as set forth herein may be made without departing from the spirit and scope thereof, and, therefore, only such limitations should be imposed as are indicated in the claims set out below.

I claim:

1. An improved, noncatalytic process for the preparation of N-(tertiaryaminoalkyl)acrylamides which comprises subjecting a β-amino propionamide to a temperature of about 180° C. to about 300° C. in the absence of a catalyst after the β-amino propionamide has been stored in a holding tank at a temperature of about 120° C. to about 240° C. and a pressure of about 300 mm Hg to about 1550 mm Hg for approximately eight to seventy-two hours.

2. The process of claim 1 wherein the N-(tertiaryaminoalkyl)acrylamides are of the formula:

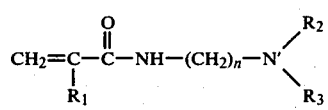

where $R_1$ is H or methyl; n is an integer from 2 to 6; and $R_2$ and $R_3$ taken singly are lower alkyl groups containing 1 to 4 carbon atoms or $R_2$ and $R_3$ taken jointly are combined with the N' atom to form a heterocyclic group selected from the group consisting of morpholine, pyrrolidine or piperidine ring groups; and the β-amino propionamide is of the formula:

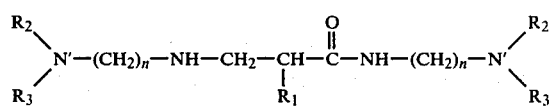

where $R_1$, n, $R_2$ and $R_3$ are the same as above.

3. The process described in claim 1 wherein the β-amino propionamide is obtained from mixing and reacting at least two moles of a tertiaryaminoalkyl amine with one mole of an acrylic acid or ester compound.

4. The process described in claim 3 wherein the tertiaryaminoalkyl amine is of the formula:

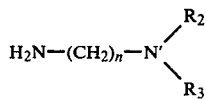

where n is an integer from 2 to 6, $R_2$ and $R_3$ taken singly are lower alkyl groups containing 1 to 4 carbon atoms, or $R_2$ and $R_3$ taken jointly are combined with the N′ atoms to form a heterocyclic group selected from the group consisting of morpholine, pyrrolidine or piperidine ring groups; and wherein the acrylic acid or ester compound is of the formula:

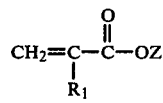

where $R_1$ is H or methyl and Z is H or an alkyl group containing 1 or 2 carbon atoms.

5. The process described in claims 1 or 3 wherein the β-aminopropionamide is subjected to a temperature of about 160° to about 210° C. while it is stored in the holding tank before it is subjected to pyrolysis to form the N-(tertiaryaminoalkyl)acrylamide.

6. The process described in claims 1 or 3 wherein the β-aminopropionamide is subjected to a pressure of about 1 atmosphere while it is stored in the holding tank before it is pyrolyzed to form the N-(tertiaryaminoalkyl)acrylamide product.

7. The process described in claims 1 or 3 wherein the N-(tertiaryaminoalkyl)acrylamide is dimethylaminopropyl methylacrylamide, dimethylaminopropyl acrylamide or N,3-isopropylaminopropyl methylacrylamide.

8. The process described in claim 1 in which the holding tank is equipped with a partial reflux condenser attached to a vent on the holding tank.

9. The process described in claim 1 in which an internal or external tank heater is used with the holding tank to maintain its temperature.

10. An improved, non catalytic process for the preparation of N-(tertiaryaminoalkyl)acrylamides of the formula

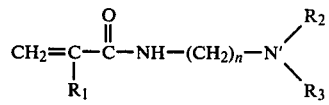

where $R_1$ is H or methyl; n is an integer from 2 to 6; and $R_2$ and $R_3$ taken singly are lower alkyl groups containing 1 to 4 carbon atoms or $R_2$ and $R_3$ taken jointly are combined with the N′ atom to form a heterocyclic group selected from the group consisting of morpholine, pyrrolidine or piperidine ring groups;

which process comprises a combination of the steps of (a) mixing and reacting at least 2 moles of a tertiaryaminoalkyl amine of the formula

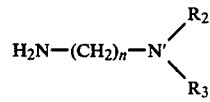

where n, $R_2$ and $R_3$ are as defined above, with an acrylic acid or ester compound of the formula

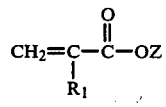

where $R_1$ is H or methyl and Z is H or an alkyl group containing 1 to 2 carbon atoms, at a temperature within the range of about 20° C. to about 200° C. to produce a β-aminopropionamide of the formula

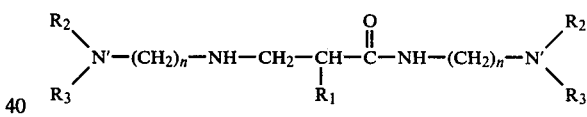

where n, $R_1$, $R_2$ and $R_3$ are the same as above;

(b) subjecting the β-aminopropionamide to a temperature of about 180° C. to about 300° C. in the absence of a catalyst; and (c) separating the resultant product N-(tertiaryaminoalkyl)acrylamide compounds;

the improvement comprising:

(d) storing the β-aminopropionamide intermediate in a holding tank at a temperature of about 120° C. to about 240° C. and a pressure of 300 mmHg to about 1550 mmHg for approximately eight to seventy-two hours after step (a) producing the β-aminopropionamide and before step (b) wherein the β-aminopropionamide is pyrolyzed to the acrylamide product.

* * * * *